United States Patent [19]
Yamazaki et al.

[11] Patent Number: 5,810,758
[45] Date of Patent: Sep. 22, 1998

[54] PURGE SOLUTION CIRCULATING APPARATUS FOR ARTIFICIAL ORGAN

[75] Inventors: Kenji Yamazaki, Pittsburgh, Pa.; Toshio Mori, Chino; Masanori Hori, Suwa, both of Japan

[73] Assignee: Sun Medical Technology Research Corporation, Japan

[21] Appl. No.: 856,518

[22] Filed: May 15, 1997

Related U.S. Application Data

[63] Continuation-in-part of Ser. No. 652,241, May 23, 1996, abandoned.

[51] Int. Cl.$^6$ .................................................. A61M 37/00
[52] U.S. Cl. ........................................ 604/4; 604/5; 623/3
[58] Field of Search ............................. 604/4–7; 600/16; 623/3, 12

[56] References Cited

U.S. PATENT DOCUMENTS

| | | |
|---|---|---|
| 4,135,253 | 1/1979 | Reich et al. . |
| 4,702,829 | 10/1987 | Polaschegg et al. . |
| 4,704,121 | 11/1987 | Moise ........................................... 623/3 |
| 4,846,152 | 7/1989 | Wampler et al. ............................ 623/3 |
| 4,927,407 | 5/1990 | Dorman . |
| 5,147,388 | 9/1992 | Yamazaki . |
| 5,290,227 | 3/1994 | Pasque ........................................ 623/3 |
| 5,300,015 | 4/1994 | Runge ......................................... 623/3 |
| 5,336,165 | 8/1994 | Twardowski . |
| 5,376,114 | 12/1994 | Jarvik ........................................... 623/3 |
| 5,437,601 | 8/1995 | Runge .......................................... 623/3 |
| 5,498,340 | 3/1996 | Granger et al. ............................. 604/4 |
| 5,531,789 | 7/1996 | Yamazaki et al. . |

FOREIGN PATENT DOCUMENTS 0659443 6/1995 European Pat. Off. .

*Primary Examiner*—John D. Yasko
*Attorney, Agent, or Firm*—Nixon & Vanderhye

[57] ABSTRACT

An apparatus for circulating a purge solution in an artificial organ has an ultrafiltration filter or reverse osmosis filter in a purge solution circulation route to inhibit passage of substances having molecular weights of 340,000 or more. A portion of the purge solution circulated by a purge solution circulation pump is passed through this filter to remove proteins that have mixed in the purge solution. The purge solution free from the proteins is supplied and circulated through the artificial organ. Proteins that have externally mixed in the purge solution can be prevented from coagulating and depositing on a seal mechanism and the like of the artificial organ.

15 Claims, 9 Drawing Sheets

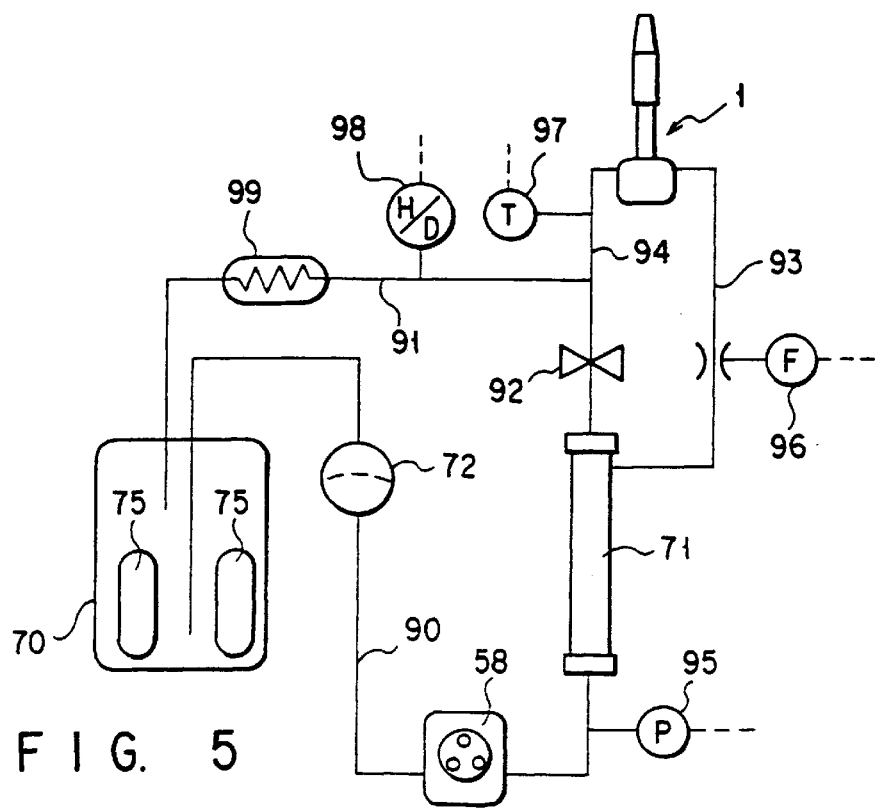
F I G. 5
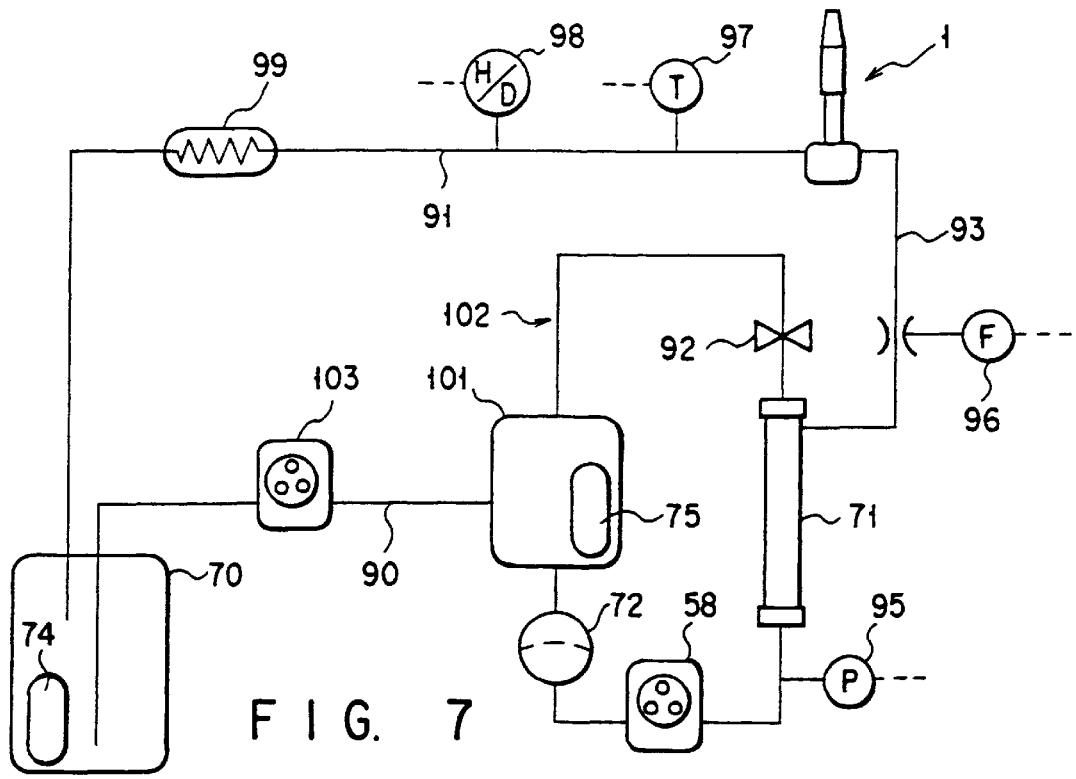
F I G. 7

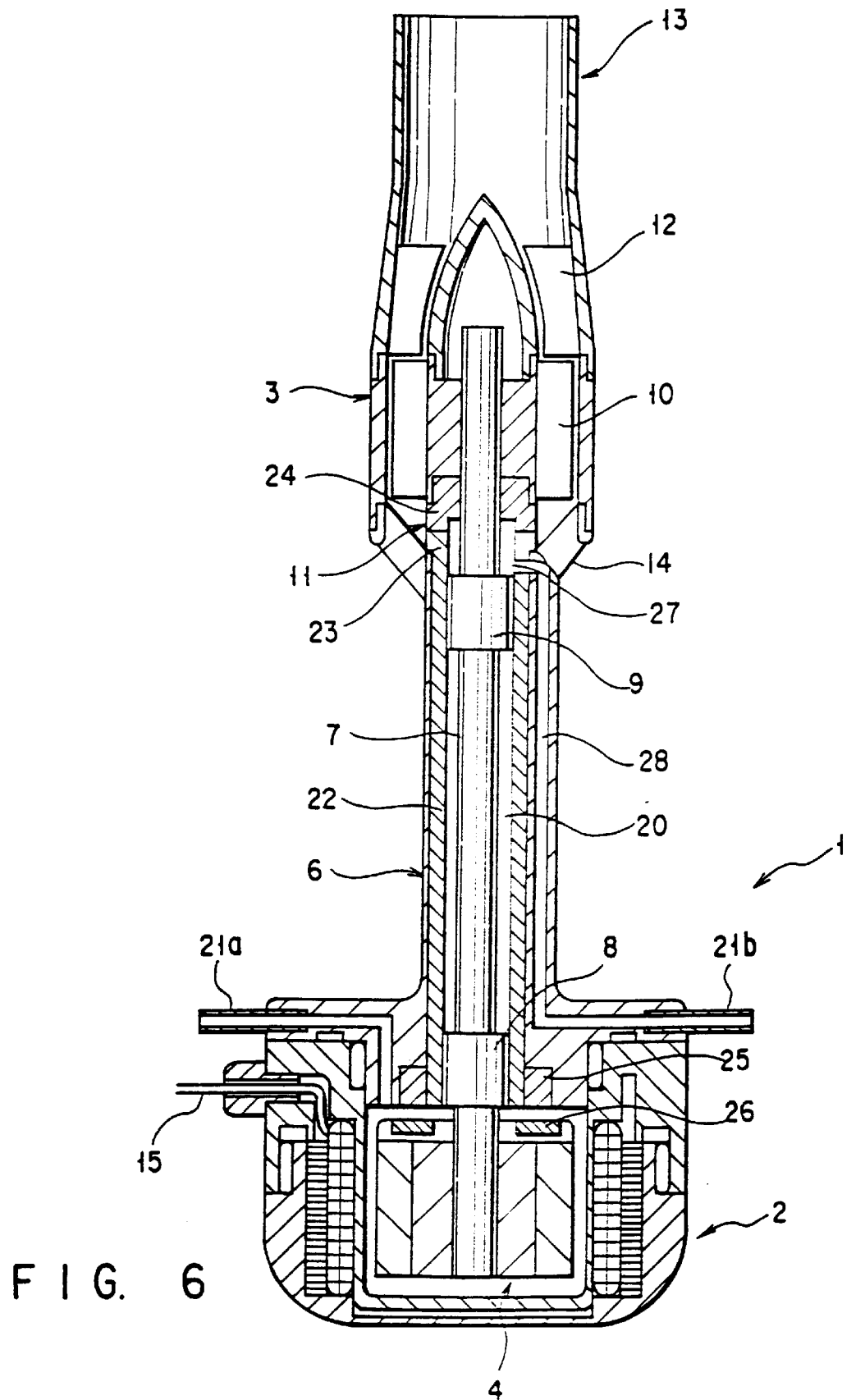
F I G. 6

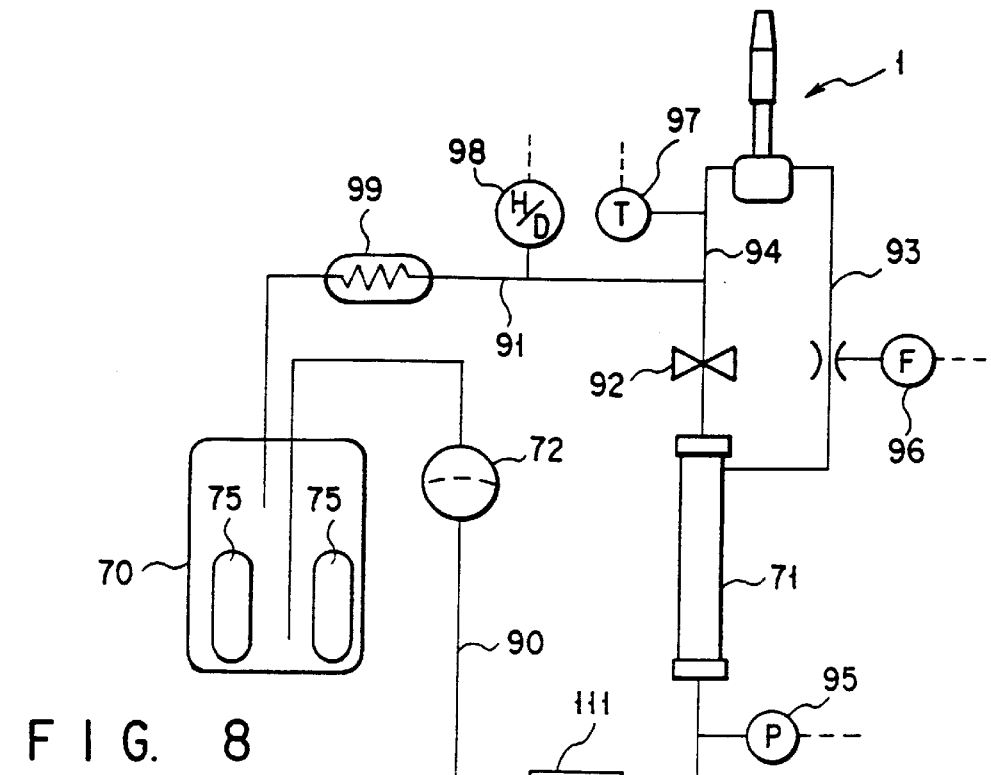
F I G. 8
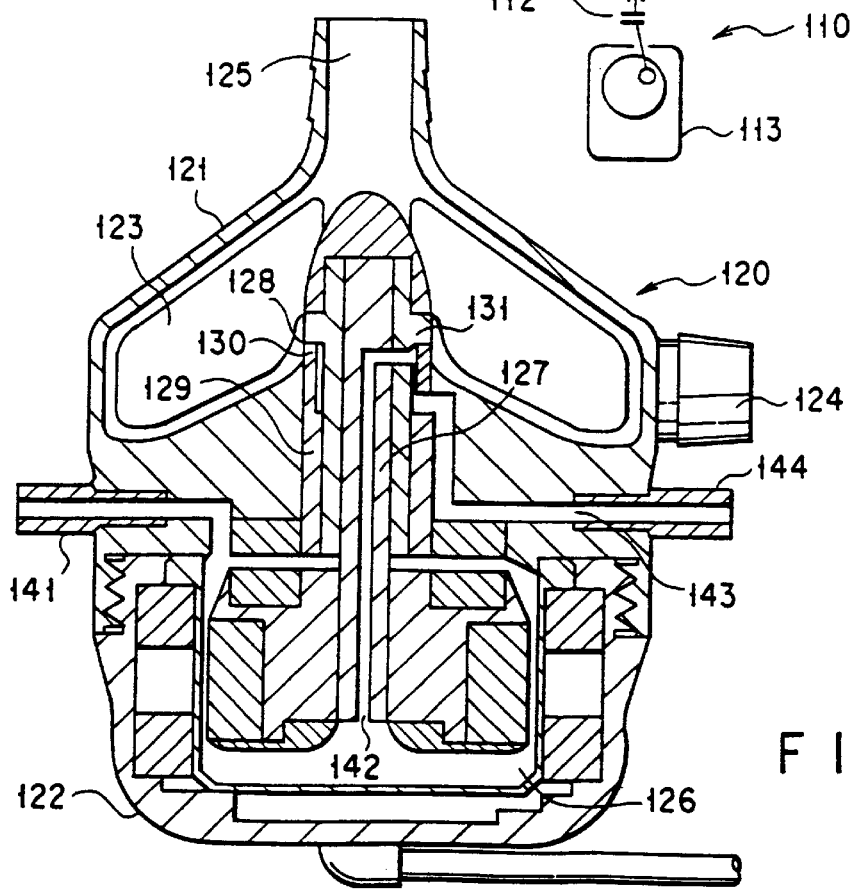
F I G. 9

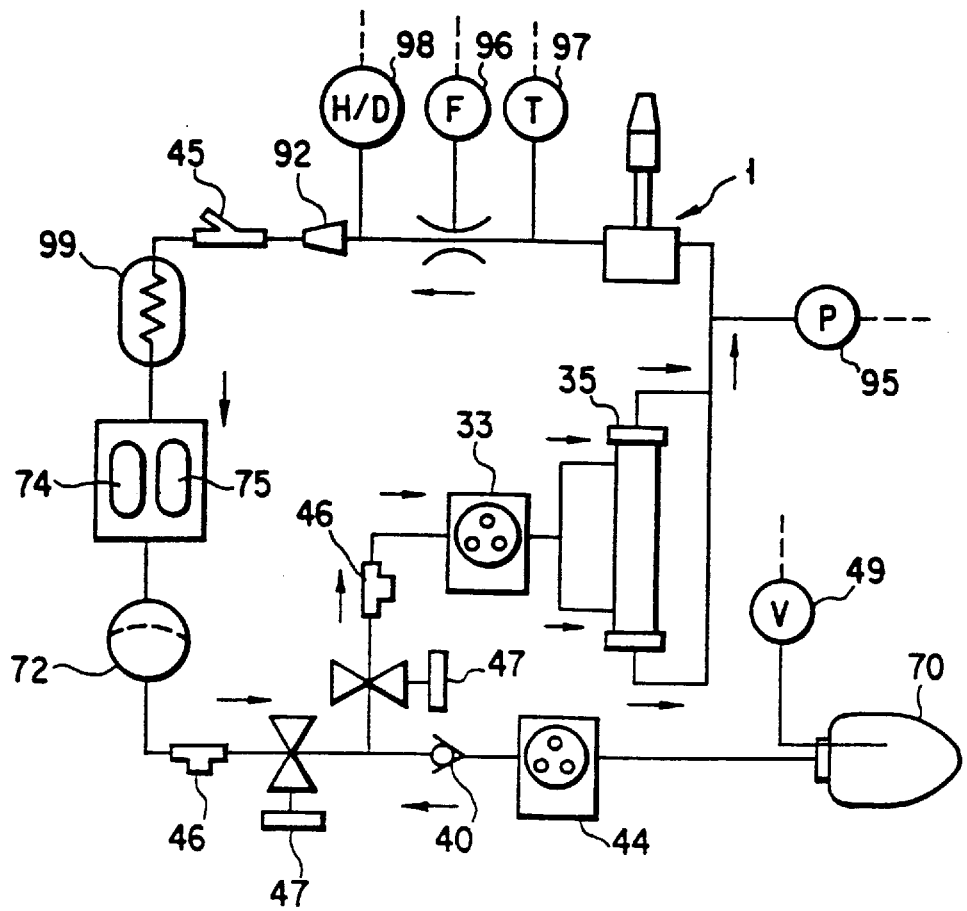
F I G. 12
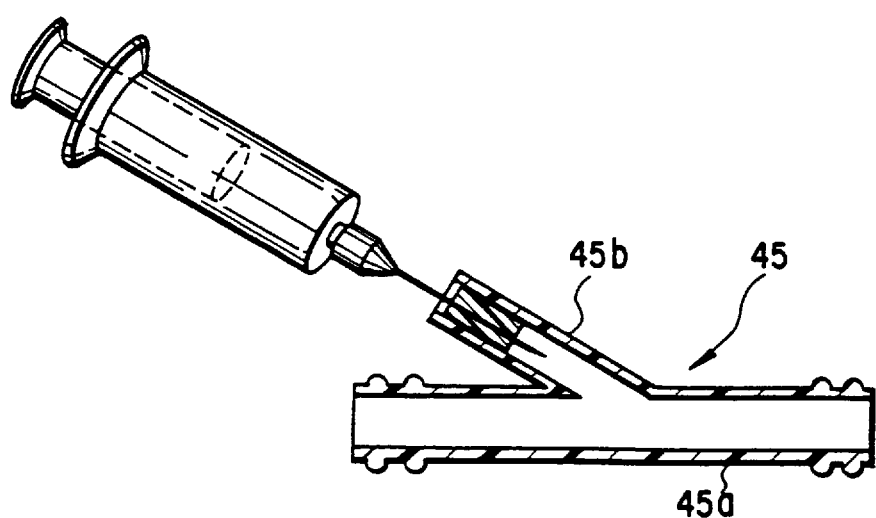
F I G. 14

PURGE SOLUTION CIRCULATING APPARATUS FOR ARTIFICIAL ORGAN

CROSS-REFERENCE TO RELATED APPLICATIONS

This application is a continuation-in-part of U.S. patent application Ser. No. 08/652,241, filed May 23, 1996 now abandoned.

BACKGROUND OF THE INVENTION

The present invention relates to an apparatus for circulating a purge solution through the interior of an artificial heart, a heart-lung machine, or any other heart-organ machine (to be called artificial organ hereinafter). More specifically, the present invention relates to an apparatus for circulating a purge solution for performing sealing maintenance, lubrication, and cooling of an artificial organ, wherein proteins that have mixed from human blood, body fluids, and the like into this purge solution can be removed, these proteins can be prevented from attaching and depositing on the seal mechanism of the artificial organ, and this purge solution can be properly disinfected.

Conventionally, a purge solution consisting of physiological saline or the like is circulated in the interior of an artificial organ such as an artificial heart, to lubricate and cool the seal mechanism of the artificial heart, and at the same time, to prevent external blood or the like from entering into this artificial heart.

In long-time use, however, proteins in blood may mix into this purge solution due to diffusion or the like. When proteins mix into the purge solution in this manner, they coagulate and deposit on the seal surface or the like of a seal mechanism. The sealing properties of the seal mechanism then degrade, and leakage of this purge solution outside the artificial heart increases, thereby increasing the consumption of the purge solution, In order to prevent this drawback, proteolytic enzymes are conventionally added to this purge solution to prevent coagulation of proteins that have mixed in the purge solution, These proteolytic enzymes, however, have a narrow range of active temperature and a limited period of time during which they act effectively.

Countermeasures for achieving disinfection to destroy bacteria, viruses, and bacterial toxins that have mixed in such a purge solution must also be taken, as a matter of course.

BRIEF SUMMARY OF THE INVENTION

The present invention has been made in consideration of the above situation, and has as its object to provide an apparatus for circulating a purge solution, wherein proteins that have mixed in a purge solution passed and circulated through an artificial organ such as an artificial heart can be properly removed, and the degradation of the sealing properties which is caused by coagulation and deposition of proteins can be properly prevented.

It is another object of the present invention to provide an apparatus for circulating a purge solution, wherein the proteins in the purge solution can be properly removed, us described above, and at the same time, bacteria, viruses, and bacterial toxins that have mixed in the purge solution can be properly destroyed by disinfection.

In order to achieve the above object, the present invention comprises a purge solution circulation path for circulating a purge solution between the above artificial organ and a reservoir which stores the purge solution, a purge solution circulation pump for circulating the purge solution through the purge solution circulation path, a protein removal filter arranged between the circulation pump and the above artificial organ and having a protein removal filter consisting of an ultrafiltration filter or reverse osmosis filter for removing proteins that have mixed in the purge solution, The ultrafiltration filter or reverse osmosis filter can filter and remove substances having molecular weights of up to several hundreds. Most of the proteins that have mixed from blood or the like to the purge solution have molecular weights of 10,000 or more. The use of such an ultrafiltration filter or reverse osmosis filter allows proper removal of most of the proteins, thereby properly preventing coagulation and deposition of these proteins, The ultrafiltration filter can filter out substances having molecular weights of 1 to 10 nm, and the reverse osmosis filter can filter out substances having molecular weights of 1 nm or less, Since viruses have sizes of 10 to 100 nm, and bacteria have sizes of 1 to 10 $\mu$m, the ultrafiltration filter or reverse osmosis filter can also remove the bacteria and viruses.

According to an embodiment of the present invention, there is provided disinfectant adding means for adding a disinfectant to the purge solution, and the protein removal filter has a pore size which allows passage of the disinfectant and does not allow passage of fibrinogen.

The disinfectant is added from the disinfectant adding means to the purge solution, and this disinfectant passes through the filter and circulates together with the purge solution. The proteins, bacteria, viruses, and the like in the purge solution are captured by this filter, and the captured bacteria and viruses are destroyed by disinfection with the disinfectant. Bacteria and viruses which have not been captured can be also destroyed with this disinfectant, thereby assuring safety.

According to another embodiment of the present invention, the disinfectant is hypochlorous acid or elctrolytic strong acid solution, and the protein removal filter is an ultrafiltration filter having a pore size which does not allow passage of substances having molecular weights of 340,000 or more, The above-mentioned electrolytic strong acid solution can be prepared by the following procedure. That is, an electrical current is applied to water so as to generate hydrogen ions and hydroxide ions, and the water containings these ions is separated by a filtration film into acidic water containing hydrogen ions and basic water containing hydroxide ions.

The main protein component which mixes in from human blood and coagulates is fibrinogen. The filter capable of capturing a substance having a molecular weight of 340,000 can almost perfectly capture fibrinogen. The filter having this pore size can also capture and remove bacteria and viruses. On the other hand, since hypochlorous acid (HOCl) has a molecular weight of about several tens, it Can properly pass through the filter and diffuses into the purge solution. Hypochlorous acid having even a low concentration can destroy most of the contemplated bacteria and viruses, and at the same time most of hypochlorous acid is stopped at the zeal portion, preventing it from entering the living body, thus making it possible to avoid the consumption of the purge solution, and adverse affect to the living body. In particular, the electrolytic strong acid solution has a pH value of as low as 2.7 or less, and an oxidation-reduction voltage or +1000 mV, at which bacteria can hardly live. Further, the solution contains a safe amount on chlorine, and therefore is exhibits a high bacterium-removing effect and a safety in a living body.

Since the electrolytic strong acid solution does not essentially contain substances having large molecular amounts, and therefore the solution certainly permeate the filter.

Proteins, bacteria, and viruses can be properly removed. The pore size of the filter is not excessively small to minimize clogging of the filter. When this filter is combined with hypochlorous acid, perfect disinfection can be achieved.

According to still another embodiment of the present invention, the purge solution circulation path comprises a cross flow circulation path for circulating the purge solution between the reservoir and the protein removal filter, and a filtration circulation path for circulating, through the artificial organ, the purge solution having passed through the protein removal filter.

The cross flow of the purge solution prevents concentration polarization on the surface of the filtration membrane of this filter and can prevent clogging of this filter. When a hollow fiber membrane filter is used in this filter, air trapping in this filter can be properly prevented by this cross flow. If a circulation tube or the like connected to this artificial organ should be bent or clamped by external objects to clog, the purge solution circulates through the cross flow circulation path. Therefore, the circulation path of the purge solution will not be broken by pressure build-up.

According to still another embodiment of the present inventions the purge solution circulation path comprises the reservoir and an end flow circulation path for circulating a purge solution between the protein removal filter and the artificial organ.

With this structure, most of the impurities contained in the circulation path is filtrated due to the end flow of the purge solution, and therefore the removal efficiency is enhanced. Further, it suffices only if the amount of the purge flow should be as much as that for the circulation path, thus making it possible to minimize the amount of the purge solution. Furthermore, since the circulation cycle is shortened, the filtration efficiency of the filter is improved.

Alternatively, when this embodiment employs a double end flow type structure in which there are a plurality of inlets and outlets, for example, two inlets and two outlets which are connected together, the pressure loss of the filter can be reduced, and one of the outlets can be used as an air discharge hole. In addition to the above, in the case where one of the inlets is used as a discard opening for the purge solution circulating in the path, the cleaning of the filter can be carried out by reversing the flow direction to the usual one. Further, in the case where the inlets and outlets are arranged in parallel to each other in the circulation path, the filter can be exchanged without pausing the operation.

According to still another embodiment of the present invention, there is provided coagulant adding means for adding a protein coagulant in a purge solution circulating in the cross flow circulation path. In this case, the cross flow circulation path has a coagulated protein removal filter for trapping coagulated protein particles. The proteins that have mixed in the purge solution are caused to coagulate with this protein coagulant to have a large size, so that the coagulated protein particles can be trapped by the coagulated protein removal filter. For this reason, the load on the protein removal filter can be reduced, and clogging can be effectively prevented, According to still another embodiment of the present invention, tho purge solution circulation pump is a roller pump, and the reservoir and the protein removal filter are formed in an integral exchange unit. The tube of the roller pump is integrally connected to the exchange unit. Since this tube is detachably connected to the roller head of the roller pump, the exchange unit and the tube are integrally detachable.

According to still another embodiment, the purge solution circulation pump is a diaphragm pump, and this diaphragm pump comprises a diaphragm portion including a diaphragm, and a driving unit arranged detachably from the diaphragm portion to reciprocate the diaphragm. The reservoir and the protein removal filter are formed in an integral exchange unit. The diaphragm portion is integrally mounted in this exchange unit. When the diaphragm portion is detached from the driving unit, the exchange unit is integrally detachable together with the diaphragm portion.

In each structure described above, the exchange unit can be integrally exchanged. In addition, the tube or diaphragm portion can be formed integrally with the exchange unit. In maintenance, exchange, or the like, contamination and leakage of the purge solution in the exchange unit can be prevented, thereby facilitating maintenance and exchange. At the same time, management of the exchange unit can also be facilitated.

According to still another embodiment of the present invention, a pressurizing unit connected to the exchange unit, for applying a static pressure on the purge solution, is made as a separate member from the purge pump unit, and the pressurizing unit is provided between the reservoir and an ultrafiltration filter, or between the artificial organ and an ultrafiltration filter, and the whole apparatus is made as a sealed type. With this structure, the pressure loss of the purge solution can be compensated for, and the pressure can be maintained at constant. Further, the reverse flow of the blood to the purge solution side can be prevented, and the exchange cycle of the filter can be prolonged. In addition, the contact of the blood components onto the slide surface of the mechanical seal 15 can be lightened, thus making it possible to prolong the life of the seal.

Further, the pressurizing unit includes a linear-type propelling means capable of reciprocal movement, and it serve also as a reservoir, and can apply pressure when needed, and detect the remaining amount of the reservoir without being in contact with the purge solution.

According to still another embodiment of the present invention, at least one sampling port having a passage for purge solution and a solution sampling piece, which are formed into Y-letter shape, is provided in the purge solution circulation path, and an elastic member is mounted into the solution sampling piece. The replenishment of the purge solution, the exchange, sampling, testing, analysis, pressurization, disinfection and the like can be carried out via the solution sampling piece without pausing the function of the apparatus during the operation of the circulation of the purge solution.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 5 is a schematic view of a purge solution circulation path;

FIG. 6 is a longitudinal sectional view of an artificial heart according to the first embodiment;

FIG. 7 is a schematic view of a purge solution circulation path according to the second embodiment;

FIG. 8 is a schematic view of a purge solution circulation path according to the third embodiment;

FIG. 9 is a longitudinal sectional view of an artificial heart of another form;

FIG. 12 is a schematic view of a purge solution circulation route according to the sixth embodiment of the present invention;

FIG. 14 is a sectional view of a sampling port in the above embodiment.

DETAILED DESCRIPTION OF THE INVENTION

The preferred embodiments of the present invention will be described with reference to the accompanying drawings. These embodiments will exemplify the purge solution circulating apparatuses for artificial hearts, but the present invention is also applicable as a purge solution circulating apparatus for a heart-lung machine or another artificial organ. For any artificial organ, the arrangement of the purge solution circulating apparatus remains almost the same.

Figure 1:
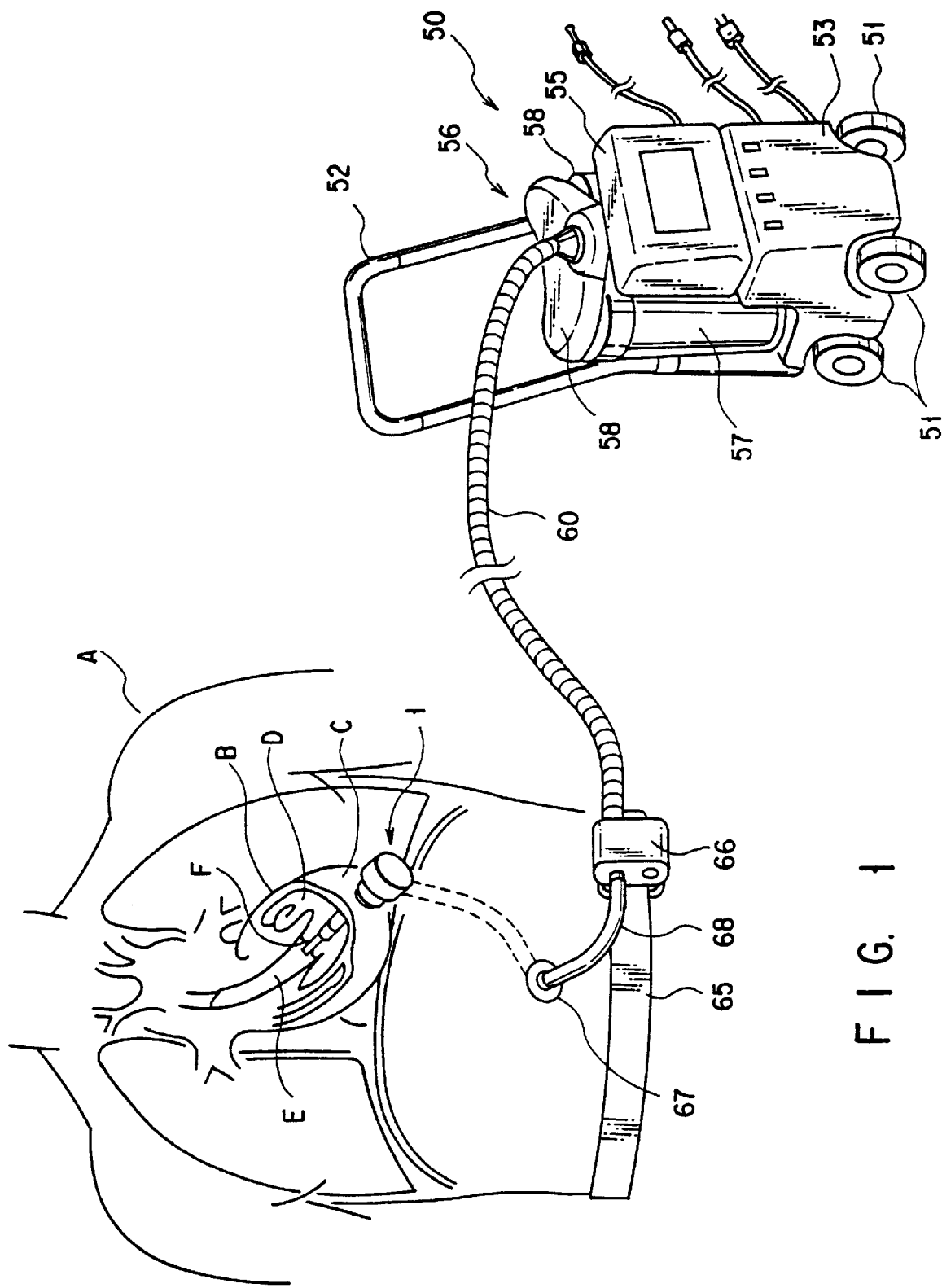
FIG. 1 is a schematic view showing the overall arrangement of a purge solution circulating apparatus for an artificial heart according to the first embodiment of the present invention.

FIGS. 1 to 6 show the first embodiment of the present invention. An artificial heart connected to this purge solution circulating apparatus will be described with reference to FIGS. 1 to 6. An artificial heart 1 is an assistant artificial heart implanted in a patient's body, does not interfere with heartbeats of the human heart, and assists supply of a short blood amount because the blood amount is short by blood supply with only heartbeats. The artificial heart 1 comprises a driving unit 2 and a pump unit 3, as shown in FIG. 6. A nozzle 13 extends from the distal end portion of the pump unit 4. As shown in FIG. 1, the pump unit 3 of the artificial heart 1 is inserted into a ventricle, e.g., a left ventricle D through an apex portion C of a heart B of a human body A, and the nozzle 13 at the distal end portion of the pump unit 4 is inserted into an aorta E through an aortic valve F. The pump unit 3 is driven by the driving unit 2 to draw and compress blood from the left ventricle D and supply blood to the aorta E from the nozzle 13 inserted past the aortic valve F.

In the artificial heart 1, the pump unit 3 inserted into the left ventricle D has a small volume. The artificial heart 1 does not interfere with the natural heartbeats of the heart B and supplies the short blood amount directly to aorta E.

The internal structure of the artificial heart 1 will be described with reference to FIG. 6. A canned motor 4 is incorporated in the driving unit 2 and driven with an external power through an electric cable 15. A driving shaft 7 of the motor 4 extends through a cylindrical portion 6 and drives the pump unit 3 arranged at the distal end portion of the cylindrical portion 6. A rotor to and a stator 12 are arranged in the pump unit 3. The rotor 10 is connected to the distal end portion of the driving shaft 7 to draw blood from the left ventricle D through a suction port 14 and compresses and supplies blood from the distal end of the nozzle 13 to the aorta E.

A purge solution containing, e.g., physiological saline as the major component is circulated inside the artificial heart 1. The artificial heart 1 is so arranged as to prevent blood and body fluids from entering therein, and the purge solution lubricates and cools the interior of the artificial heart 1. An inlet 21a and an outlet 21b for the purge solution are formed in the driving unit 2 of the artificial heart 1. The inlet 21a and the outlet 21b are connected to a purge solution circulating apparatus (to be described later) through a flexible supply tube and a flexible return tube (neither is shown).

A seal mechanism of the driving shaft 7 is arranged in the artificial heart 1. This seal mechanism comprises, e.g., a mechanical seal mechanism 11. The mechanical seal mechanism 11 comprises an outer cylindrical member 22 made of a ceramic material. A seal ring portion 23 is integrally formed with the distal end portion of the outer cylindrical member 22. The outer cylindrical member 22 extends through the cylindrical portion 6. The driving shaft 7 extends through the outer cylindrical member 22. A follow ring 24 made of a ceramic material or carbon composite material is in tight contact with the end face of the seal ring portion 23. The follow ring 24 is mounted on the driving shaft 7. Note that permanent magnet 25 and 26 are arranged on the stator and rotor sides of the motor 4 in the driving unit 2. An axial load acts on tho driving shaft 7 in accordance with the repulsion of these permanent magnets, so that the follow ring 24 is in tight contact with the seal ring portion 23 at a predetermined pressure.

The interior of the outer cylindrical member 22 constitutes a purge solution chamber 20. The driving shaft 7 is rotatably supported on the inner surface of the outer cylindrical member 22 through bearings 8 and 9. Dynamic pressure grooves (not shown) are formed on the outer surfaces of the bearings 8 and 9. When the bearings 8 and 9 rotate together with the driving shaft 7, the purge solution in the purge solution chamber 20 is supplied to the sliding surface between the seal ring 23 and the follow ring 24.

In this artificial heart 1, the purge solution is supplied from the inlet 21a to the driving unit 2 and lubricates and cools the motor 4 in the driving unit 2. The purge solution then passes through the purge solution chamber 20 and is supplied to the sliding surface between the seal ring unit 23 and the follow ring 24 of the mechanical seal mechanism 11. The sliding surface is lubricated and cooled with the supplied purge solution: A small amount of the blood components may diffuse via the sliding surface into the artificial heart. The blood components are washed down with the purge solution circulating in the artificial heart. Eventually they are discharged from the artificial heart, along with the purge solution, through the return path 28 and the outlet 21b. Thus, the blood components, which are diffused in the artificial heart, are reliably prevented from being deposited on the internal surface and respective parts of the artificial heart, including bearings and motor.

A return port 27 is formed at the distal end portion of the outer cylindrical member 21b. This return port 27 communicates with a return path 28 formed along the cylindrical portion 6. The return path 28 also communicates with the outlet 22. The purge solution supplied to the sliding surface at the distal end portion of the outer cylindrical member 22 is discharged outside the artificial heart through the return port 27, the return path 28, and the outlet 22b except for the purge solution portion flowing outside the artificial heart. The purge solution circulates through the above route in the artificial heart.

The artificial heart 1 is cooled, lubricated, and maintained for sealing properties with the purge solution circulated inside the artificial heart 1. However, proteins continuously enter, albeit in a very small amount, from the outside, i.e., blood to the purge solution due to diffusion or the like. When the entered proteins accumulate in the circulating purge solution, they coagulate and deposit on the sliding surface of the mechanical seal mechanism 11 to degrade the sealing properties and undesirably increase the flow rate of the purge solution flowing outside the artificial heart, i.e., the consumption amount of the purge solution. In addition, the proteins coagulate to form protein particles, and these protein particles may deposit on the respective parts of the artificial heart, or clog the purge solution flow path. In order to prevent such a drawback in the artificial heart, the sectional areas of the flow paths are sequentially increases in the order of the inlet 21a, the flow path in the driving unit 2, the purge solution chamber 20, the return port 27, the return path 28, and the outlet 21b. A possibility of the coagulated protein particles clogging the artificial heart is eliminated.

Figure 2:
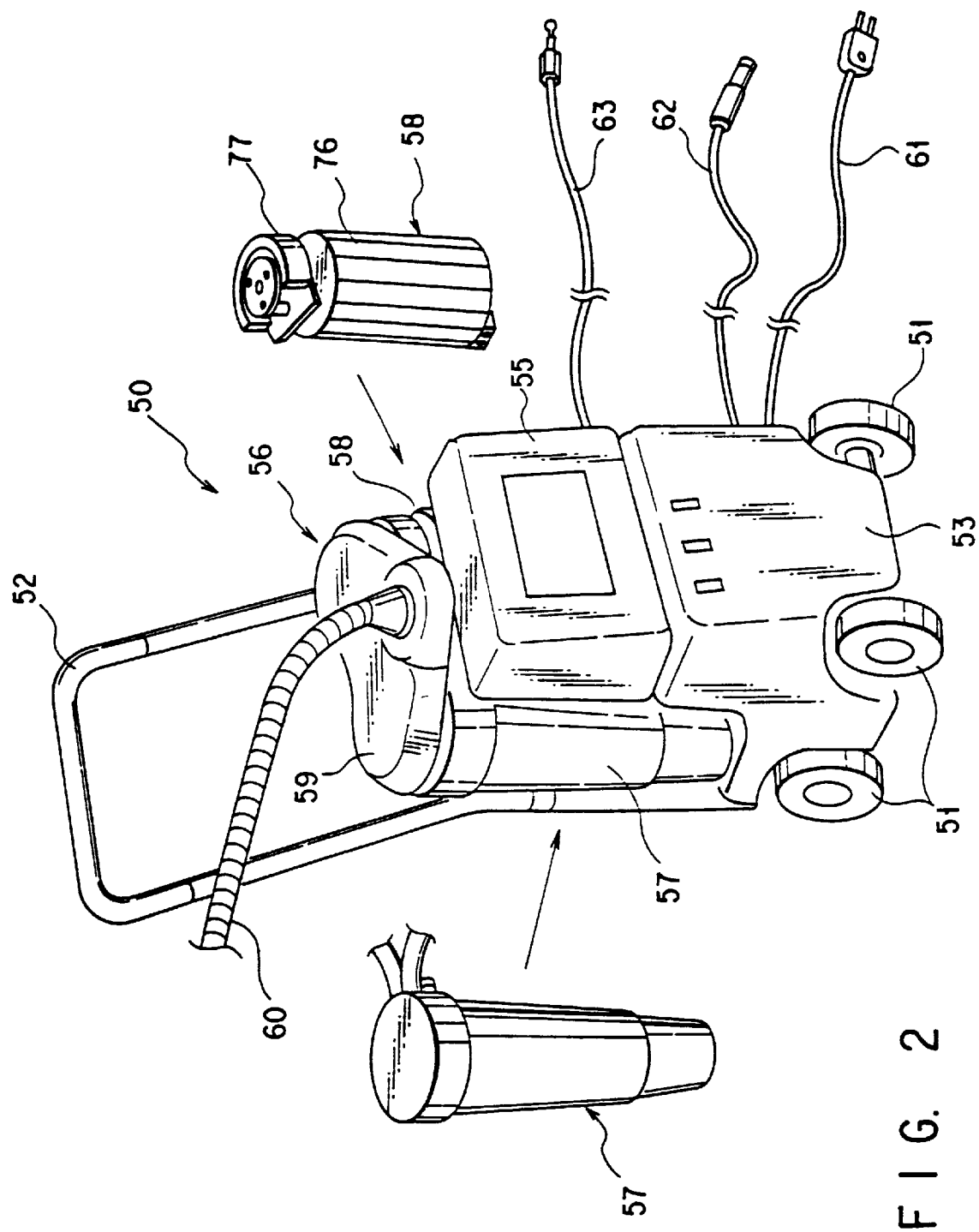
FIG. 2 is a perspective view showing the main body of the purge solution circulating apparatus according to the first embodiment.

An apparatus for circulating the above purge solution in the interior of the artificial heart 1 described above will be described below. FIGS. 1 and 2 show the schematic arrangement of this apparatus. Reference numeral 50 denotes a main body of the purge solution circulating apparatus. The main body 50 is a portable body having wheels 51 and a handle 52. A power supply unit 53, a control unit 55, and a mounting unit 56 are arranged in the main body 50. An exchange unit 57 and a purge solution circulation pump, i.e., a purge pump unit 58 can be detachably mounted in the mounting unit 56.

A battery such as a lithium battery is incorporated in the power supply unit 53 to supply power to drive the artificial heart 1, power to drive the purge pump unit 58 of the purge solution circulating apparatus, and any other power. Note that a charger is incorporated in the power supply unit 53, and an AC outlet cord 61 connected to an external commercial power supply and a vehicle power cord 62 connected to a power supply such as an automobile battery through the cigarette lighter of an automobile are arranged in the power supply unit 53. The artificial heart 1 and the circulating apparatus are powered from an external power supply through the cord 61 or 62. When the artificial heart 1 and the circulating apparatus cannot be powered due to movement, they can be powered by the battery incorporated in the power supply unit 53. Note that the battery incorporated in the power supply unit 53 has a capacity for continuously supplying power to the components for 12 hours without any external power supply, The control unit 55 incorporates an electronic circuit such as a microchip and controls and monitors the overall operation of this purge solution circulating apparatus and the operating state of the above artificial heart 1. Note that a telephone connection cord 63 to be connected to a telephone line is connected to the control unit 55 to allow communication with a hospital computer through a communication line such as a telephone line or the Internet. The above monitor and control operations can be performed under the control of the hospital computer.

Equipments required for circulating the purge solution are incorporated as a unit in the exchange unit 57 described above. The purge solution can be circulated between the circulating apparatus and the artificial heart 1 by the purge pump unit 58. Note that a connection hose 60 extends from the mounting unit 56 and is connected to another connection tube 68 through a connector 65 mounted on a human body A with a belt 65. The connection tube 68 is guided to the body cavity of the human body through a skin button 67 implanted in the human body A and is connected to the driving unit 2 of the artificial heart 1. The connection hose 60 and the connection tube 68 are tubes made of a flexible material and incorporate a supply tube connected to the inlet 21a of the artificial heart 1, a return tube connected to the outlet 21b, the electric cable 15 for supplying power to the motor 4 of the artificial heart 1, and the like.

The purge solution circulation system of the purge solution circulating apparatus will be described with reference to FIGS. 1 and 2 and FIGS. 3 to 5. The exchange unit 57 has a housing 70, and the interior of the housing 70 substantially constitutes a reservoir which stores the purge solution. The housing 70 incorporates various types of equipments constituting the circulating routes of the purge solution, thereby forming paths in which the purge solution flows. More specifically, the housing 70 incorporates a protein removal filter 71, a coagulated protein removal filter 72, an ultraviolet lamp 73 for disinfecting the purge solution, a disinfectant slow delivery capsule 74, a protein coagulant slow delivery capsule 75, and other equipments. The paths for causing these equipments to communicate with each other are also formed. Note that these equipments and the communication routes will be described in detail later. The housing is preferably made of a transparent material and allows the operator to visually check the state of the purge solution stored therein.

Figure 3:
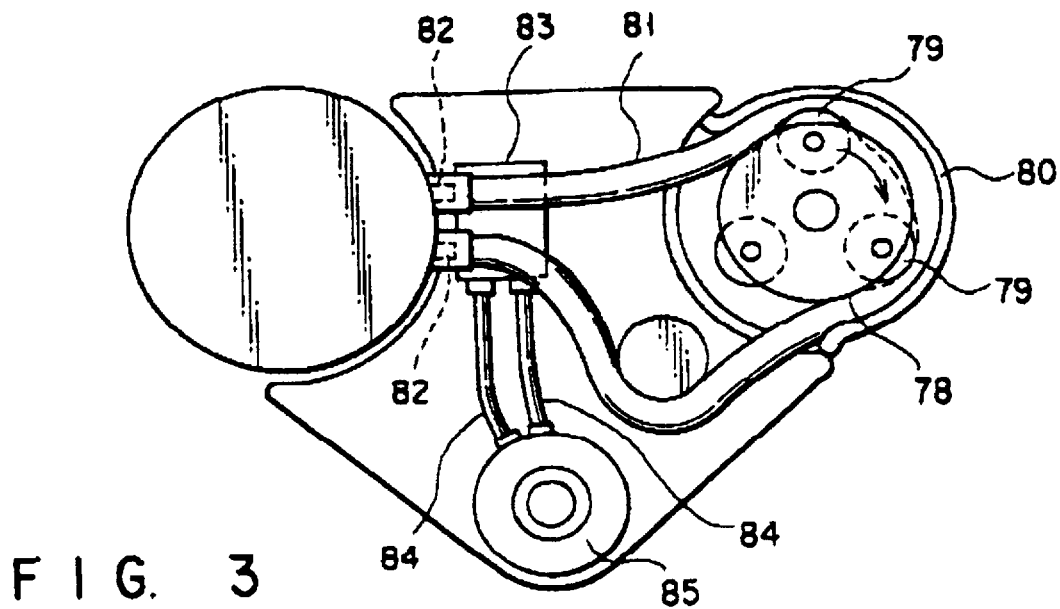
FIG. 3 is a plan view of a mounting unit of the main body.
Figure 4:
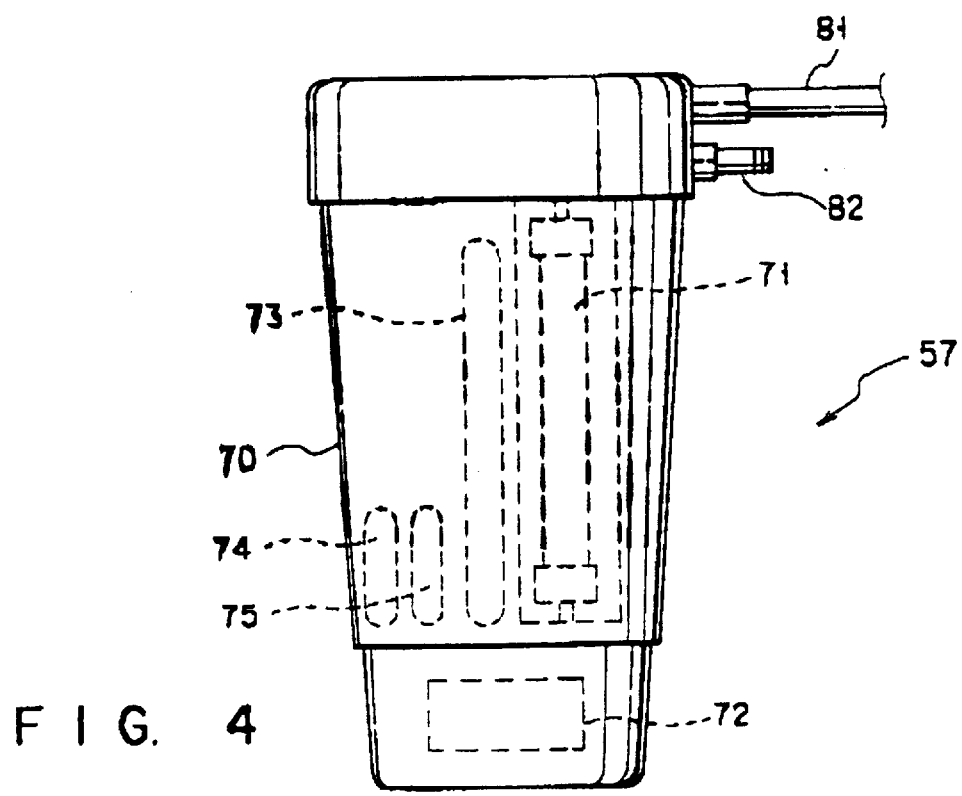
FIG. 4 is a side view of an exchange unit.

The purge pump unit 58 is a roller pump in this embodiment. The purge pump unit 58 comprises a roller head unit 77 and a driving unit 76 incorporating a motor, a reduction gear, and the like. The roller head unit 77 comprises 4 rotary disk 78 and a plurality of rollers 79 rotatably disposed along the edge of the rotary disk 78, as shown in FIG. 3. When this rotary disk 78 is rotated, a tube 81 made of an elastic material is clamped between the rollers 79 and an arcuated guide wall 80, thereby supplying the purge solution in the tube 81. The tube 81 is arranged integrally with the exchange unit 57. In attaching or detaching the exchange unit 57 to or from the apparatus, the tube 81 is attached to or detached from the roller head unit 77, so that the tube 81 can be attached to or detached from the roller head unit 77 together with the exchange unit 57.

A supply/return solution connector 82 for the purge solution is arranged in the exchange unit 57. A solution socket 83 connected to the solution connector 82 is arranged in the mounting unit 56. The solution connector 82 is detachably connected to the solution socket 83. The solution socket 83 is also connected to a head 85 through a tube 84. The connection hose 60 is connected to the head 85. The tube 84 is connected to the tube in the connection hose 60 through the head 85. Therefore, the purge solution can be circulated between the exchange unit 57 and the artificial heart 1 through the solution connector 82, the solution socket 83, and the connection hose 60.

The solution connector 82 has a valve mechanism for automatically closing the connector 82 upon disconnection from the solution socket 83. A contamination prevention cover or the like is mounted on the solution socket 83. A new purge solution and new filters, and the like are supplied as an exchange unit 57 in a sealed state, so that a patient can easily replace the old exchange unit with a new exchange unit.

Electrical connectors are incorporated in the head 85, and the electric cable 15 incorporated in the connection hose 60 is connected to the power supply unit 53 in the main body 50, thereby supplying the driving power to the artificial heart 1. The upper surface of the mounting unit 56 is covered with a detachable cover 59.

The circulating routes of the purge solution will be described with reference to FIG. 5. FIG. 5 is a schematic view showing a state in which the layout of each equipment and each circulating route is different from the actual layout, and they are incorporated in the exchange unit 57, as described above.

The reservoir 70 is constituted by the housing of the exchange unit 57. A predetermined amount of purge solution is stored in the reservoir 70. The purge solution consists of physiological saline as its major component, or pure water can also be used as the purge solution. The purge solution in the reservoir 70 is supplied to the purge pump unit 58 through a cross flow supply path 90. The purge solution is compressed by the purge pump unit to a predetermined pressure, and the compressed purge solution is supplied to the protein removal filter 71. Note that part of the cross flow supply path 90 is, of course, constituted by the tube 81 of the roller pump.

The protein removal filter 71 comprises, e.g., an ultrafiltration filter made of a hollow fiber membrane. The filter 71 has a pore size which does not allow passage of substances having molecular weights of 340,000 or more. The supplied purge solution flows through, e.g., the hollow fiber membrane. That is, the purge solution flows through the protein removal filter 71 in a so-called cross flow state. The purge solution flowing out of the protein removal filter 71 returns to the reservoir 70 through a cross flow return path 91. The cross flow supply path 90 and the cross flow return path 91 constitute the cross flow circulating route of the purge solution. The purge solution is circulated through this route.

A portion of the purge solution is filtered through the protein removal filter 71 and supplied to the artificial heart 1 through a filtration/circulation supply path 93. The purge solution circulated in the artificial heart 1 merges midway along the cross flow return path 91 through a filtration/circulation return path 94 and then returns to the reservoir 70. The filtration/circulation supply path 93 and the filtration/circulation return path 94 constitute a filtration/circulation route. The purge solution filtered through the protein removal filter 71 is circulated through this route. The filtration/circulation supply path 93 and the filtration/circulation return path 93 are constituted by the solution connector 82, the tube 84, the connection hose 60, and the like, as described above.

A restrictor mechanism 92 is disposed at the outlet side of the protein removal filter 71 of the cross flow return path 91. This restrictor mechanism 92 applies a predetermined flow resistance to the purge solution cross-flowing through the protein removal filter 71, maintains the internal pressure of the protein removal filter 71 at a predetermined pressure, and controls the flow rate of the purge solution filtered through the protein removal filter 71 and supplied to the artificial heart 1 through the filtration/circulation supply path 93. The restrictor mechanism 92 may be located at any place in the circulation path, and is capable of maintaining the pressure at the place where it is provided, at predetermined one.

The restrictor mechanism 92 appropriately sets the flow rate of the purge solution so that the purge solution fed by the purge pump unit 58 is circulated in the cross flow supply and return paths 90 and 91 at a sufficient flow rate to prevent damage to the purge pump unit 58 and each circulation route even if the tubes constituting the filtration/circulation supply path 93 and the filtration/circulation return path 94 are bent or clamped between obstacles to clog. The restrictor mechanism 92 may be a normal valve mechanism. However, a choke tube having a smooth diameter-reduced inner surface may be used as the restrictor mechanism to prevent coagulated proteins from depositing on a valve body, in a valve clearance, and on other portions. In this case, the inner diameter of the choke tube can be set on the basis of various tests.

Figure 10:
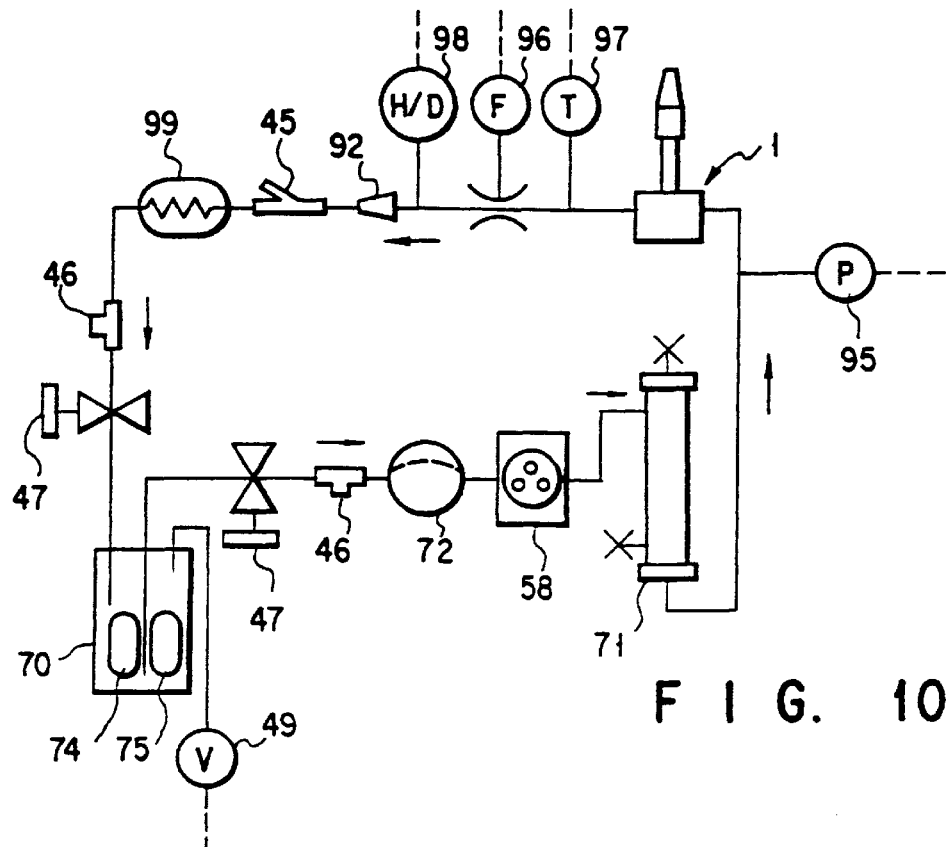
FIG. 10 is a schematic view of a purge solution circulation route according to the fourth embodiment of the present invention.

In the case where the amount of the blood components leaking from the sealed portion, is sufficiently small, the filteration mode of the end flow method may be used as can be seen in FIG. 10. In this case, most of the impurities can be filtrated when the amount of the blood components in the purge solution within the circulation path is small, thus increasing the removal efficiency.

When the purge solution is circulated in the artificial heart 1, proteins mix in the purge solution due to diffusion. Of the proteins mixed into the purge solution from the blood, fibrinogen coagulates and deposit at the movable parts of the artificial heart, such as bearings, impairing the function of the movable parts. The fibrinogen has a molecular weight of 340,000. Most of the fibrinogen components can be removed by the protein removal filter 71 using an ultrafiltration filter having a pore size of 340,000. The pore size of the protein removal filter 71 is set to a necessary value for removing fibrinogen. Fibrinogen can be properly removed, and clogging can be minimized.

As described above, in this purge solution circulating apparatus, the purge solution from which fibrinogen is removed by the protein removal filter 71 is supplied to the artificial heart 1. For this reason, proteins will not coagulate and deposit on the mechanical seal mechanism and other portions of the artificial heart 1, thereby preventing degradation of these components and properly maintaining the function of the artificial heart 1 for a long period of time.

Since the purge solution flows through the protein removal filter via the cross flow circulation route in a cross flow state, the surface of the filter membrane of the protein removal filter 71 is prevented from generating concentration polarization, thereby preventing clogging of this filter.

The disinfectant slow delivery capsule 74 is accommodated in the reservoir 70 as a disinfectant adding means, A capsule of a drug delivery system available from Arza, U.S.A. is used as the disinfectant slow delivery capsule 74. A solution such as an electrolytic solution is sealed in the capsule. A small bag of a drug sealed in the capsule is collapsed by the osmosis of an external solution permeating into the capsule through a semipermeable membrane, and the drug such as a disinfectant in the bag is slowly delivered in a predetermined amount outside the capsule. In this embodiment, the disinfectant is hypochlorous acid, e.g., sodium hypochlorate (NaOCl). Sodium hypochlorate is slowly delivered such that the concentration of the purge solution is kept at 0.05 to 2.0 ppm for about a month. It should be noted that a strong acid electrolytic solution can be used as the disinfectant, and it is also possible that the disinfection is carried out not continuously but intermittently at the replacement of the reservoir.

The delivered disinfectant, i.e., sodium hyperchlorate diffuses in the purge solution and passes through the protein removal filter 71 because this sodium hypochlorite has a molecular weight of about several tens. This sodium hypochlorite also diffuses in the purge solution flowing through the paths 93 and 94. The sodium hypochlorite is used in the entire purge solution to kill bacteria and viruses. The protein removal filter 71 captures a lot or bacteria and viruses in addition to fibrinogen, These bacteria and viruses are killed by sodium hypochlorite. In the purge solution circulating apparatus of this embodiment, the bacteria and viruses are captured by the protein removal filter, and at the same time disinfection using sodium hypochlorate can be performed. Contamination of the purge solution can be properly prevented, and highly safe purge solution circulation is assured. The sodium hypochlorite contained in the purge solution has an extremely low concentration, and the purge solution scarcely leaks from the artificial heart into a living body. Should the purge solution leaks into the living body, the hypochlorate acid system contained in the solution, such as sodium hypochlorite, would combine with an organic material in the living body, producing a nontoxic organic chlorine compound. This would ensure safely of the living body.

The protein coagulant slow delivery capsule 75 is accommodated in the reservoir 70. As for the capsule 75, a protein coagulant is sealed in a capsule as in the capsule 74, and the protein coagulant is slowly delivered in a predetermined amount. The fibrinogen that have mixed in the purge solution coagulates to form particles. The coagulated protein removal filter 72 is arranged midway along the cross flow supply path 90. The coagulated protein removal filter 72 is a normal filter to capture the coagulated protein particles described above. Most of the proteins such as fibrinogen that have mixed in the purge solution can be removed, and the load on the protein removal filter 71 can be reduced, thereby effectively preventing clogging of the filter.

A variety of detectors for managing the purge solution and the operation of the purge solution circulating apparatus are arranged in the purge solution circulation routes. More specifically, a pressure detector 95 for detecting the pressure of the purge solution is arranged in the downstream of the purge pump unit 58. A slow rate detector 96 is arranged midway along the filtration/circulation supply path 93 to detect the flow rate of the purge solution supplied to the artificial heart 1. A temperature detector 97 is arranged midway along the filtration/ circulation return path 94 to detect the temperature of the purge solution discharged from the artificial heart 1. A blood detector 98 is arranged midway along the cross flow return path 91 to detect blood that has mixed in the purge solution. It should be noted that the detectors 95, 96, 97 and 98 are not limited to the above-described positions, but they may be situated at appropriate positions of the circulation path in accordance with the operation state of the purge solution circulation apparatus.

Signals from the detectors 95, 96, 97, and 98 are supplied to the control unit 55 to monitor and control the state of the purge solution and the operating state of the purge solution circulating apparatus.

Since the purge solution circulating route is constituted by the cross flow supply and return paths 90 and 91, a large amount of purge solution is circulated in the cross flow supply and return paths 90 and 91 to cool the purge solution, thereby effectively preventing an increase in temperature of the purge solution.

When the purge solution circulating apparatus is used in a hot place, a cooler 99 is arranged, as needed. This cooler 99 is a compact cooler including a Peltier affect element. When the temperature of the circulated purge solution reaches a predetermined temperature or more, the cooler 99 cools the purge solution and maintains it at the predetermined temperature.

Although not illustrated in FIG. 5, the ultra-violet lamp 73 is arranged in the reservoir. The ultraviolet lamp 73 is turned on, as needed, to disinfect the purge solution in the reservoir 70.

The present invention is not limited to the first embodiment. For example, FIG. 7 shows a purge solution circulating apparatus according to the second embodiment.

In this embodiment, a second reservoir 101 is arranged in addition to a first reservoir 70, and a second cross flow circulation route 102 is formed in addition to first cross flow supply and return paths 90 and 91. The purge solution is circulated between the second reservoir 101 and a protein removal filter 71 through the second cross flow circulation route 102. Note that the purge solution is fed from the first reservoir 70 to the first reservoir 101 by a feed pump 103 in this embodiment. A protein coagulant slow delivery capsule 75 is accommodated in the second reservoir 101.

In this embodiment, the purge solution circulated through an artificial heart 1 and the purge solution circulated in the second cross flow circulation route 102 flow in perfectly different systems. For example, the purge solution containing the protein coagulant discharge from the capsule 75 is circulated within only the second cross flow circulation route 102. The characteristic feature of this embodiment is to facilitate management of the purge solution. The purge solution circulating apparatus of the second embodiment is substantially the same as that of the first embodiment except for the above arrangement. The same reference numerals as in FIG. 1 denote the same parts in FIG. 7, and a detailed description thereof will be omitted.

FIG. 8 shows a purge solution circulating apparatus according to the third embodiment of the present invention. In this embodiment, a diaphragm pump 110 is used as the purge pump unit. The diaphragm pump 110 is divided into a diaphragm unit including a diaphragm, a casing, and a valve mechanism to flow the purge solution and a driving unit 113 including a motor, a reduction gear, and a crank mechanism to drive the diaphragm unit 111. These units are detachably connected through a coupling mechanism 112.

In the third embodiment, when the coupling mechanism 112 is attached to or detached from the diaphragm unit 111, the diaphragm unit 111 can be attached to or detached from the driving unit 113 together with an exchange unit 57. Note that the purge solution circulating apparatus of the third embodiment is substantially the same as that of the first embodiment except for the above arrangement. The same reference numerals in FIG. 1 denote the same parts in FIG. 8, and a detailed description thereof will be omitted. It should be noted that the purge pump is not limited to the type described above, but, apart from the above, it may be a rotary pump, gear pump, plunger pump and the like.

The tube 81 of the roller pump unit 58 used in the first embodiment and the diaphragm unit 111 incorporated in the third embodiment are movable parts. The tube 81 or the diaphragm unit 111 may be replaced by the exchange unit 57. In this case, the tube 81 or the unit 111 is automatically replaced by a new one. Since the tube 81 and the unit 111 undergo elastic deformation to feed the purge solution, each being integral and having no sealed parts. Hence, there is no possibility that the purge solution leaks from the tube 81 or the unit 111 when either is replaced by a new one.

The purge pump unit according to the present invention is not limited to those described above. Rather, it may be a gear pump, a piston pump or any other type of a pump.

The purge solution circulating apparatus of this embodiment is also applicable as the purge solution circulating apparatus for an artificial heart of another type. For example, an artificial heart of this type is shown in FIG. 9.

This artificial heart is mounted outside the human body and comprises a pump unit 121 and a driving unit 122. An impeller 123 is incorporated in the pump unit 121, a blood inlet 125 is connected to, e.g., a ventricle of a heart through a tube or the like, and a blood outlet 124 is connected to, e.g., an aorta of a human body through a tube or the like, thereby supplying blood from the ventricle to the aorta.

A motor 126 is arranged in the driving unit 122 and connected to the impeller 123 through a driving shaft 127. A mechanical seal mechanism 128 is mounted on the distal end portion of the driving shaft 127. Reference numeral 129 denotes an outer cylindrical member made of a ceramic material; 130, a seal ring formed at the distal end portion of the outer cylindrical member 129; and 131, a follow ring. The purge solution flows in the driving unit from a purge solution inlet 141, passes through a path 142 formed at the center of the driving shaft, and is supplied to a sliding surface of the mechanical seal mechanism 128. The purge solution then passes through a return path 143 and is discharged from a purge solution outlet 144. The purge solution is circulated in this route in an artificial heart 120.

The protein removal filter according to the present invention is not limited to an ultrafiltration filter, but can be a reverse osmosis filter.

The present invention can be applied not only to the purge solution circulating apparatus for an artificial heart, but also to the purge solution circulating apparatus for a heart-lung machine or any other artificial organ.

In the above descriptions, the artificial heart of the present invention was described in connection with the case where the shaft flow pump is used, but the present invention is not limited to this type. It is naturally possible to use a centrifugal pump as shown in FIG. 9, or some other type of pump.

FIG. 10 shows a purge solution circulation apparatus according to the fourth embodiment of the present invention. The circulation apparatus of this type has a structure essentially similar to that of the purge solution circulation apparatus of the above-described embodiment, except that the purge solution is allowed to pass the protein removal filter 71 in the end flow mode.

In the purge solution circulation apparatus of the fourth embodiment, a plurality of air bleed valves 46 are provided at appropriate positions, so as to make it possible to discard air or gas mixed into the purge solution circulation system, from the system. Also, an open/close valve 47 is provided to be used when the purge solution is replaced with new one.

Further, the purge solution circulation apparatus of this embodiment is provided with a sampling port 45. The sampling port 45 has a structure as can be seen in FIG. 14 in cross section. As shown in the figure, the sampling port 45 has a passage 45a for the purge solution and a solution sampling piece 45b, which are formed into a Y-shape, and an elastic member is mounted into the solution sampling piece 45b. With the sampling port 45, for example, an injection needle can be applied and removed as shown in the figure, without causing leakage of the purge solution even after the needle is removed. Therefore, the replenishment of the purge solution, the exchange, sampling, testing, analysis, pressurization, disinfection and the like can be carried out via the solution sampling piece without pausing the function of the apparatus even in operation of the circulation of the purge solution.

It should be noted that the fourth embodiment has a structure similar to that of the previous embodiment except for the respect discussed above, and in FIG. 10, members corresponding to those of the previous embodiment are designated by the same reference numerals, and the descriptions therefor are omitted.

Figure 11:
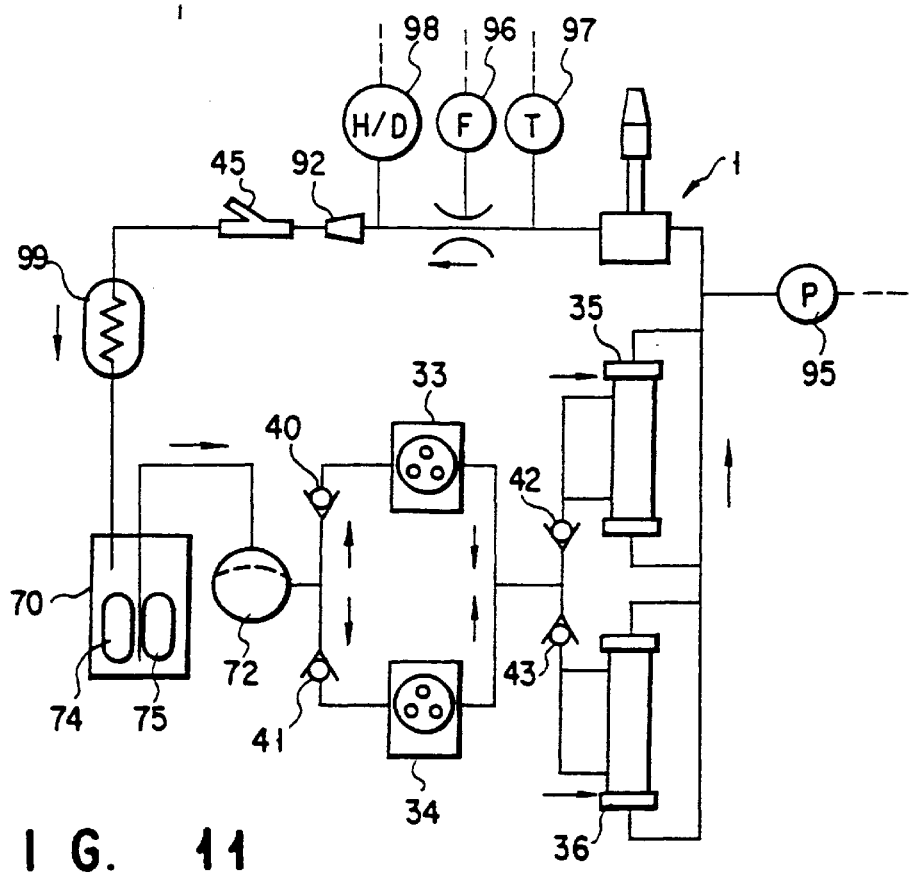
FIG. 11 is a schematic view of a purge solution circulation route according to the fifth embodiment of the present invention.

Next, a purge solution circulation path according to the fifth embodiment of the present invention will now be described with reference to FIG. 11. FIG. 11 shows a schematic view thereof, and therefore the positions of the devices and the circulation path, shown in the figure, are different from the actual positions. In reality, the devices and circulation path are set together integrally and built in the exchange unit 57.

This figure illustrates a reservoir 70 consisting of the housing of the exchange unit 57, and a predetermined amount of purge solution is reserved in the reservoir 70. The purge solution is allowed to pass a coagulated protein removal filter 72, and sent to two purge pumps 33 and 34, and the solution is sent to two protein removal filters 35 and 36 at a predetermined pressure by these purge pumps 33 and 34. The purge solution filtrated by the protein removal filters 35 and 36 is supplied into an artificial heart 1, and the purge solution circulated in the artificial heart 1 is returned to the reservoir 70. Thus, the circulation path for the purge solution is constituted, and the purge solution is circulated via the above-described path. With the double end flow type structure in which inlets and outlets of the two protein removal filters 35 and 36 are connected together, the pressure loss of the filter can be reduced, and one of the outlet can be used as an air bleed opening. Further, in the case where one of the inlets is used as a purge solution discarding opening in the circulation path, the cleaning of the filter can be conducted at the same time by reversing the direction of flow with respect to the usual flow. Furthermore, in the case where the inlets and outlets are arranged in parallel to each other in the circulation path, the filter can be exchanged without pausing the operation.

In the case where check valves 40, 41, 42 and 43 are provided respectively for the openings of the parallel paths of the purge pumps and the filter, the counterflow of the purge solution in the circulation path can be prevented.

Further, when the purge pump 33 is provided on the upstream side of the protein removal filter 35, the purge solution from which the impurities generated from the purge pump were filtrated out, can be sent to the artificial heart 1.

Figure 13:
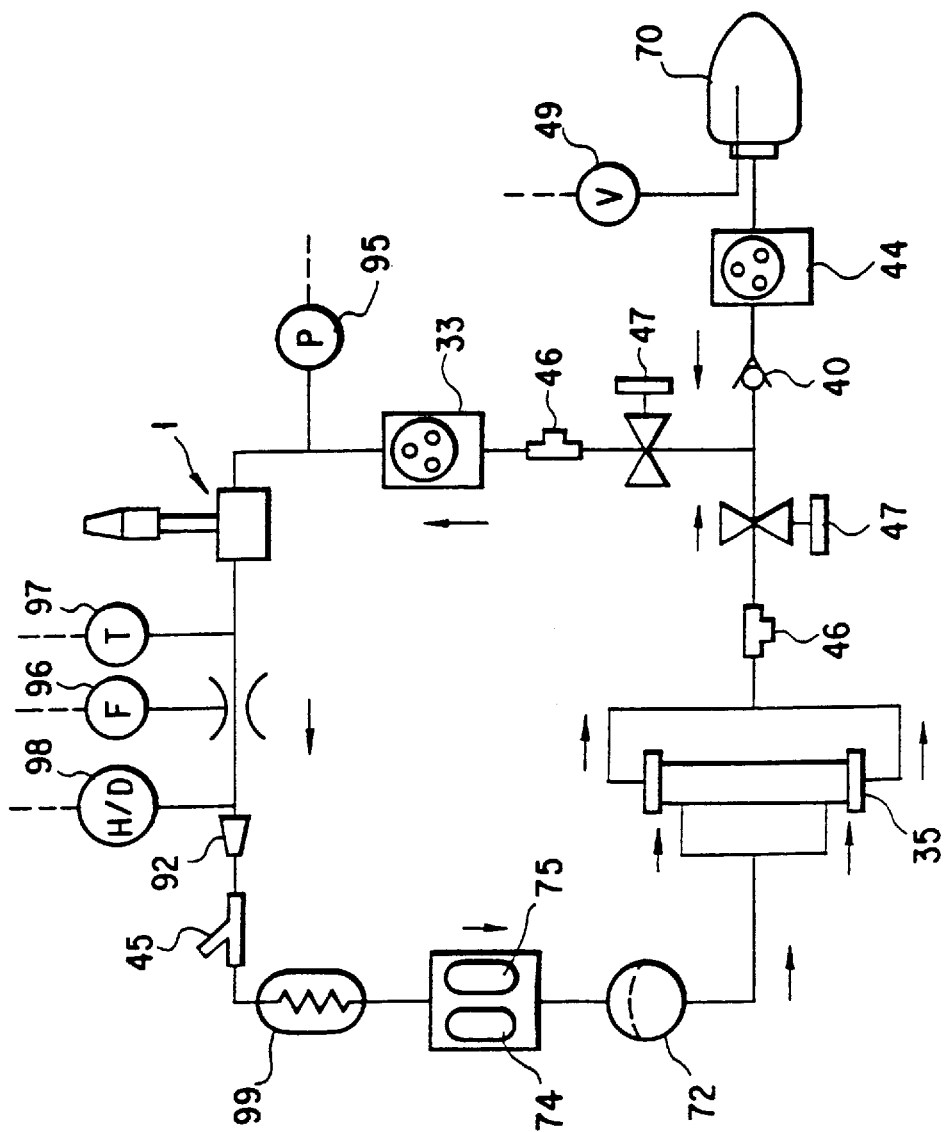
FIG. 13 is a schematic view of a purge solution circulation route according to the seventh embodiment of the present invention.

FIG. 13 shows a purge solution circulating apparatus according to the seventh embodiment of the present invention, in which the purge pump 33 is provided on the upstream side of the artificial heart 1. With this structure, the pressure loss of the purge solution, which occurs along the path to the artificial heart 1, can be reduced.

It should be noted that the reservoir is not limited to the housing 70, but may be of a pack type, tank type or the like. Further, when a remaining amount detector 49 is provided in the reservoir 70 in accordance with necessity, the amount of the remaining purge solution can be detected.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

We claim:

1. A purge solution circulating apparatus for circulating a purge solution through an interior of an artificial organ in order to lubricate and cool the interior of said artificial organ and maintain sealing properties thereof, comprising:

a disinfectant adding means for adding disinfectant to the purge solution;

a reservoir for storing purge solution;

a purge solution circulation route for circulating the purge solution between said artificial organ and the reservoir which stores the purge solution;

a purge solution circulation pump for circulating the purge solution through said purge solution circulation route; and a protein removal filter arranged in a purge solution circulation route between said purge solution circulation pump and said artificial organ, the protein removal filter includes a reverse osmosis filter capable of removing fibrinogen that has mixed in the purge solution and said protein removal filter has a pore size which allows passage of the disinfectant and does not allow passage of fibrinogen.

2. An apparatus according to claim 1, wherein the disinfectant is hypochlorous acid or electrolytic strong acid solution, and said protein removal filter comprises a reverse osmosis filter having a pore size which does not allow passage of substances having molecular weights of not less than 340,000.

3. An apparatus according to claim 1, wherein said purge solution circulation routes comprise a cross flow circulation route for circulating the purge solution between said reservoir and said protein removal filter and a filtration/circulation route for circulating, through said artificial organ, the purge solution having been filtered through said protein removal filter.

4. A purge solution circulating apparatus according to claim 3, wherein said purge solution circulating routes are end flow circulating routes for circulating the purge solution between said reservoir and said protein removal filter.

5. An apparatus according to claim 3, further comprising:

coagulant adding means for adding a protein coagulant in the purge solution circulated in said cross flow circulation route; and a coagulated protein removal filter arranged in said cross flow circulation route to filter out coagulated protein particles.

6. An apparatus according to claim 1, wherein said purge solution circulation pump is a roller pump, said reservoir and said protein removal filter are formed into an integral exchange unit, and said roller pump has a tube connected to said exchange unit such that said tube is attached to or detached from a roller head of said roller pump to integrally attach or detach said exchange unit together with said tube.

7. An apparatus according to claim 1, wherein said purge solution circulation pump is a diaphragm pump having a diaphragm unit including a diaphragm and a driving unit detachable from said diaphragm unit to reciprocate said diaphragm, said reservoir and said protein removal filter are formed in an integral exchange unit in which said diaphragm unit is integrally mounted in such a manner that said diaphragm unit is attached to or detached from said driving unit to integrally attach or detach said exchange unit together with said diaphragm unit.

8. An apparatus according to claim 7, wherein a pressure unit, connected to said exchange unit, for applying a static pressure on the purge solution, is provided as a separated member from said purge pump unit, and said apparatus as a whole is formed into a sealed type.

9. An apparatus according to claim 8, wherein said pressure unit is provided between said reservoir and said reverse osmosis filter.

10. An apparatus according to claim 8, wherein said pressure unit is provided between said artificial organ and said reverse osmosis filter.

11. An apparatus according to claim 8, wherein said pressure unit includes linear propelling means capable of reciprocal movement.

12. An apparatus according to claim 6, wherein said purge solution circulation pump is provided between said protein removal filter and said artificial organ.

13. An apparatus according to claim 1, wherein said reservoir is provided as a separated member from said purge solution circulating routes.

14. An apparatus according to claim 1, wherein at least one sampling port from which the sampling solution can be injected or sampled, is provided for at least one location of the purge solution circulating routes.

15. An apparatus according to claim 1, wherein at least one air bleed drain for air-bleeding the circulation routes, is provided for at least one location of the purge solution circulating routes.

* * * * *